US00PP08551P

United States Patent [19]

Klemm

[11] Patent Number: Plant 8,551

[45] Date of Patent: Jan. 18, 1994

[54] GERANIUM NAMED KLEFLAM

[75] Inventor: Siegfried Klemm, Stuttgart, Fed. Rep. of Germany

[73] Assignee: Klemm & Sohn, Stuttgart-Muhlausen, Fed. Rep. of Germany

[21] Appl. No.: 952,641

[22] Filed: Sep. 28, 1992

[51] Int. Cl.[5] ..... A01H 5/00

[52] U.S. Cl. ..... Plt./87.12

[58] Field of Search ..... Plt. 87.12

*Primary Examiner*—James R. Feyrer

*Attorney, Agent, or Firm*—Tilton, Fallon, Lungmus & Chestnut

[57] ABSTRACT

A new and distinctive Geranium cultivar particularly distinguished by its dark green leaves with light zonation and bicrenate border which provide a contrast to its dark red colored semidouble flowers is provided. In this Geranium a large umbel of flowers stands on strong stems of between 290 to 300 mm high, whose foliage is Botrytis resistant.

1 Drawing Sheet

BACKGROUND OF THE NEW PLANT

This Geranium cultivar originated as a hybrid seedling produced in my nursery at Stuttgart, Germany, by my crossing of two plants, hereinafter identified, selected from a field of various geranium varieties maintained at my nursery for breeding purposes. This particular seedling was selected from among the sibling population from the stated cross due to its unusually attractive flower color; the desired plant characteristics of compactness, dense canopy of lush foliage of clear green coloration and zonation which is inconspicuous to absent and highly disease resistant; self-branching from basal portions, and a high level of vigor until blooming, allowing for rapid development of flowering specimens to market stage. This selected seedling was propagated by me at Stuttgart, Germany, by cuttings with very satisfactory results and thereafter this selected plant was propagated through several successive generations in the same manner which demonstrated conclusively that the novel characteristics of the originally selected seedling would be maintained from generation to generation and its homogeneity would be firmly established.

DESCRIPTION OF THE DRAWING

My new geranium plant is illustrated by the accompanying photographic drawing which, in full color, shows the form and coloration of the flowers as they appear with relatively close spacing at the upper end portion of the flowering stem of the plant. The colors shown are as nearly true to these herein specified as is reasonably possible to obtain by conventional photographic procedures.

DESCRIPTION OF THE NEW PLANT

The following is a detailed description of my new geranium plant as observed from plants grown under greenhouse conditions in Stuttgart, Germany, with the stated flower colors being according to The R.H.S. Colour Chart of The Royal Horticultural Society of London, England.

THE PLANT

Origin: Seedling, not commercially available.

Parentage:

*Seed parent.*—Red seedling, not commercially available.

*Pollen parent.*—Matrix commercially available.

These parent plants are so identified in my business records of the present cultivar maintained at the offices of the Stuttgart, Germany, nursery and the production of the aforementioned hybrid and the stated cross and the selection of 'Kleflam' are also there recorded.

Classification:

*Botanic.*—Pelargonium Zonale-hybrid.

*Commercial.*—Zonal Geranium.

Form: A broad shaped, upright bush.

Height: About 270–290 mm.

Growth rate: Rooted cuttings rapidly attain market-stage plant stature, but growth is slowed and plant size is nearly maintained upon the onset of flowering.

Branching character: Self-branching without pinching to form a compact specimen having a foliage canopy which hides the stems of the plant.

Habit: Upright.

Main stem length: 130–160 mm.

Foliage:

*Quantity.*—50 to 60 leaves. Internode length: 12–18 mm.

*Number of leaves.*—Medium.

*Size and shape of leaf.*—45×70 mm to 60×90 mm. The leaf is runiform shaped. Zonation: 9–11 mm, dark brown.

*Margin type.*—Bicrenate.

*Texture.*—Smooth.

*Color.*—Top: RHS 147-A. Bottom: 146-A.

*Petioles.*—Length: 26 mm.

THE BUD

Size: Medium.

Shape: Ovoid to round, with pointed apex.

Diameter: 11 mm.

Length: 15 mm.

Rate of opening: Medium.

Color of petals:

*When sepals first divide.*—Red purple.

*When petals begin to unfurl.*—Dark red.

Sepals:

*Shape.*—Ovoid, pointed and standing up.

*Number.*—Five.
*Color.*—Inside — green. Outside — dark green.
Calyx:
*Shape.*—Cup shaped.
*Aspect.*—Very slightly hairy.
*Size.*—Broad.

INFLORESCENCE

Blooming habit: Profusely from spring to fall continuously.
Size of bloom: Medium.
*Diameter.*—50 mm.
*Depth.*—10 mm.
Borne: Singly one per pedicel of an umbel cluster.
Shape: Cup.
Petalage:
*Number of petals.*—Six to eight.
*Number of florets.*—40-50 per umbel.
*Form.*—Medium broad with entire margins.
*Texture.*—Soft.
*Arrangement.*—Imbricated.
*Appearance.*—Satiny.
*Color.*—Outer petals — RHS 46C on the body and base. Reverse side — RHS 46D. Inside petals — RHS 46C on the body and base. Reverse side — RHS 46D.
Petaloids:
*Number.*—Two.
*Size.*—2-5 mm.
*Color.*—RHS 46C.
Flower stem:
*Length.*—About 160 mm.
*Character.*—Erect.
*Color.*—Dark green to brown.
Discoloration after full bloom: Five to six days.
Persistence: The petals of matured flowers hang on and dry.
Lasting quality:
*On the plant.*—About 18-21 days.
*As cut flower.*—About six days.
Disease resistance: Botyrytis.

Pruning or training requirements: None. The claimed Geranium is cultivated according to the following procedure. Propagation is begun at week 2. Potting takes place in week 6. The plant is placed in 12 cm pots. The soil at that time has a pH of 6 and a EC of 1.3 to 1.4. The plant is not pinched and not treated wity Cycocel. Fertilizing begins at week 7 and is performed 5 times until week 15. Starting at week 6, the daily medium temperature in the room where the plant is maintained is set to 17° C. This is continued until week 11. In week 12, the temperature is lowered to 16° C. The following week, on a cool morning, two hours before sunrise, the room temperature is lowered an additional 6 degrees Celsius for 7 hours.

THE REPRODUCTIVE ORGANS

Stamens:
*Number.*—Seven.
*Arrangement.*—In a ring around the pistil.
*Anthers.*—Size: About 1.6 mm to 1.8 mm. Color: RHS 41C and white.
*Filaments.*—Length: About 4.5 mm. Color: Red.
*Pollen.*—Color: Orange.
Pistils:
*Number.*—One. Length: 7 mm.
*Stigmas.*—Red.
Ovaries:
*Character of ovaries.*—Normal.
*Color.*—Light green before insemination.

FRUIT

Fertility: The fruit is fertile.
Shape: Ovoid.
Color at maturity: Dark brown.

I claim:

1. A new and distinctive Geranium plant, substantially as herein shown and described, characterized by its dark red semidouble flowers in a large umbel and dark green leaves with light zonation and a bicrenate border.

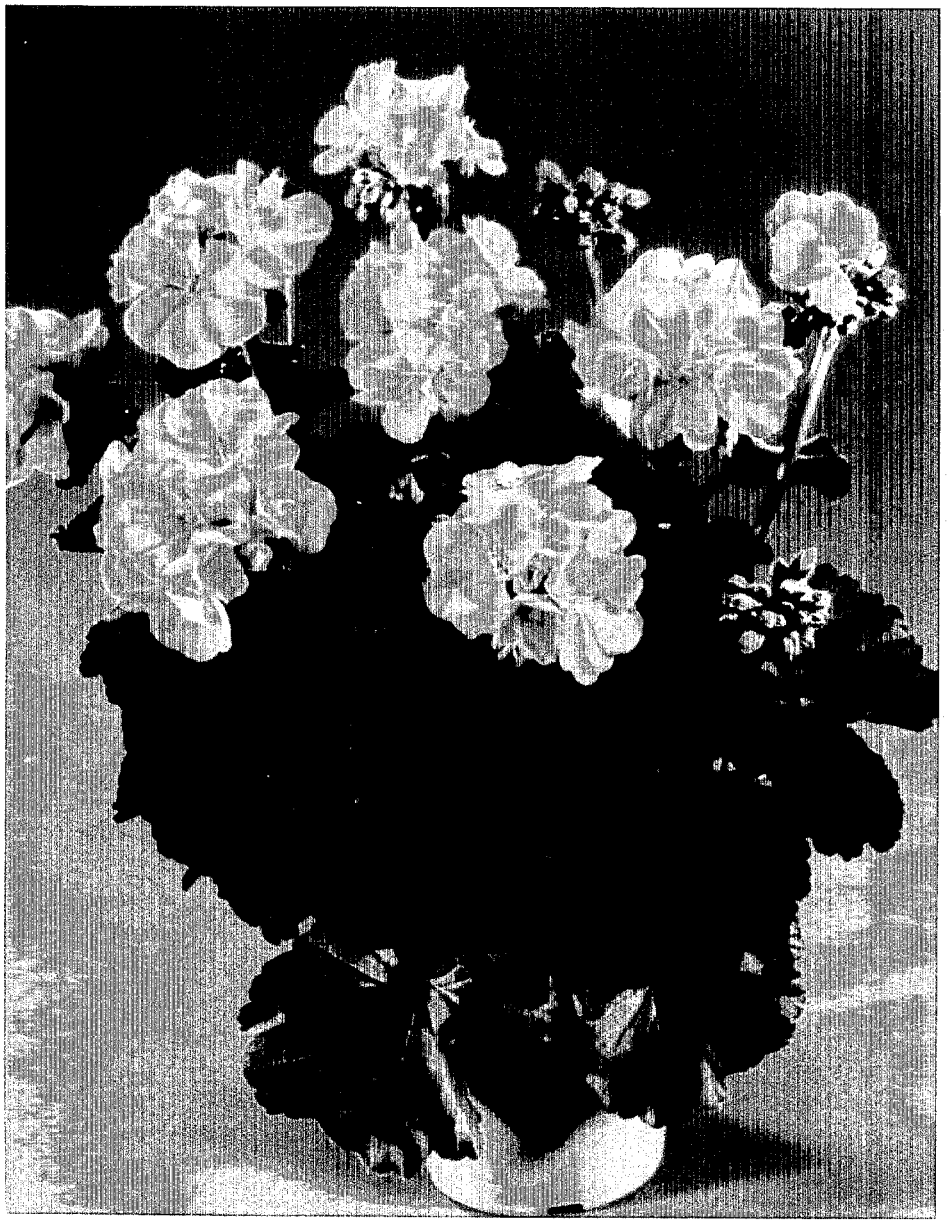

* * * * *